United States Patent [19]

Myantt

[11] Patent Number: 4,799,794

[45] Date of Patent: Jan. 24, 1989

[54] INTERIOR REFLECTIVE CHAMBER EMBODYING AN ORDERING PRINCIPAL FOR COLOR REFLECTORS THEREIN

[76] Inventor: Roy L. Myantt, 420 N. Hamilton, Ypsilanti, Mich. 48197

[21] Appl. No.: 102,119

[22] Filed: Sep. 29, 1987

[51] Int. Cl.⁴ .................. G01N 21/03; G01N 21/25
[52] U.S. Cl. ............................ 356/246; 356/414; 356/419
[58] Field of Search .............. 356/246, 409, 410, 414, 356/419

[56] References Cited

U.S. PATENT DOCUMENTS 3,797,942 3/1974 Joly ..................................... 356/410

Primary Examiner—Vincent P. McGraw
Assistant Examiner—S. A. Turner
Attorney, Agent, or Firm—James M. Deimen

[57] ABSTRACT

A color separation device or chamber in the form of a regular rhombic dodecahedron. Each interior face or plane comprises a specifically colored reflecting surface and is arranged in such a manner that each interior plane expresses the given order of reflection suggested by a syllogistic algorithm. The conventional or regular dodecahedron is circumscribed by a sphere. The chamber is suitable as a cell for liquid or gas in an analysis instrument such as a spectrophotometer. Such a chamber may be equipped with inlet and outlet ports, light sources and light sensors at appropriate locations in the interior faces.

6 Claims, 1 Drawing Sheet

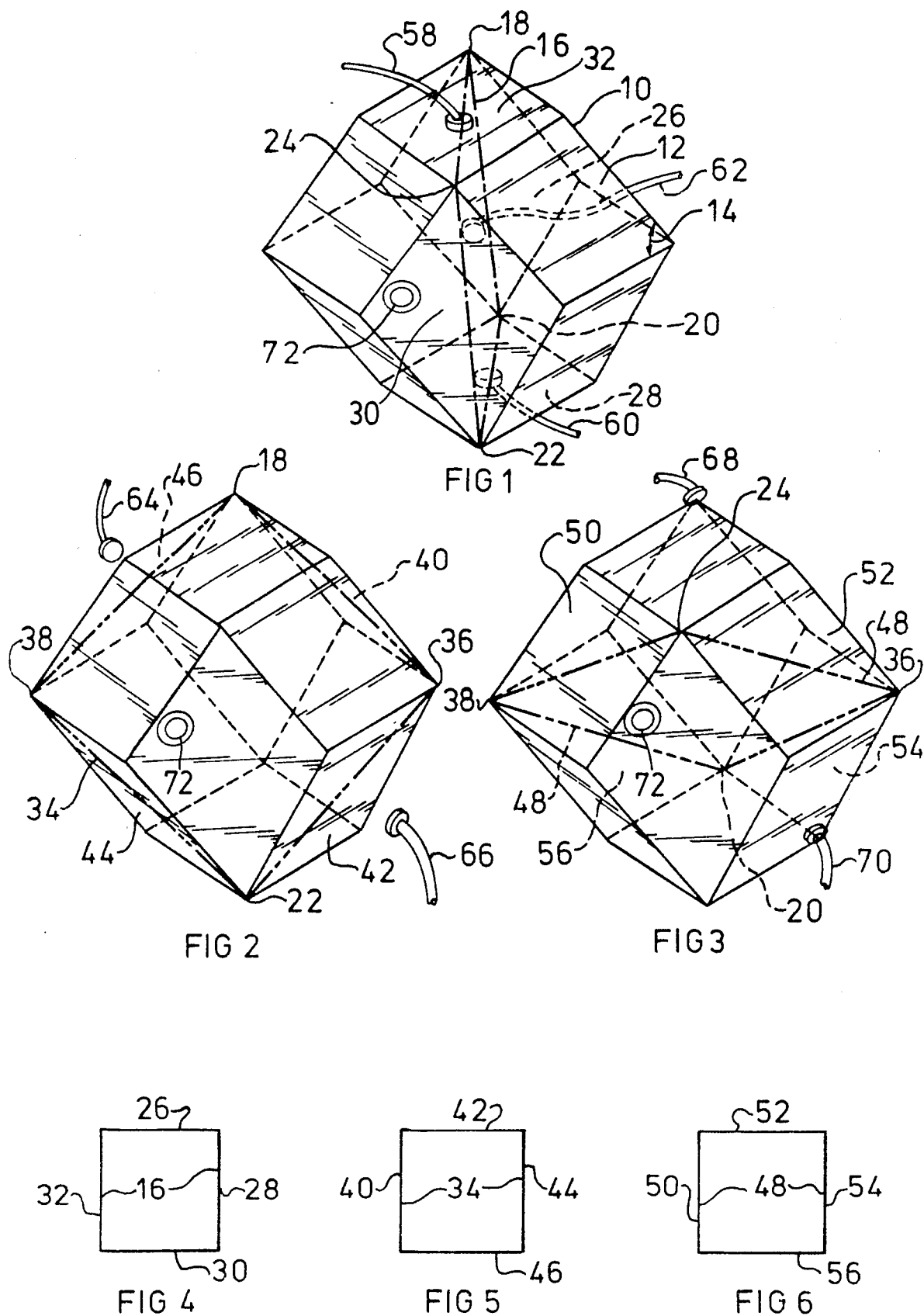

INTERIOR REFLECTIVE CHAMBER EMBODYING AN ORDERING PRINCIPAL FOR COLOR REFLECTORS THEREIN

BACKGROUND OF THE INVENTION

The field of the invention pertains to reflective color separation devices in the form of multifaceted enclosures, and, in particular, to uses for such devices in analytic instruments.

Leibniz, co-inventor of differential calculus, spent much of his life contributing to combinational theory. Among his achievements was a method to reduce certain forms of inferences to prime or non-prime relationships. An algorithm for the expression of categorical syllogisms by means of numbers was provided by Leibniz in the body of his logical papers. In particular, the algorithm pertinent hereinbelow is from Leibniz's "Rules From Which A Decision Can Be Made, By Means Of Numbers, About The Forms And Moods Of Categorical Syllogisms" published in English in *Leibniz, Logical Papers*, G. H. R. Parkinson, ed. Clarendon Press, 1966 (pp. 25–32).

Examples of analytic instruments which utilize sample chambers are disclosed in U.S. Pat. No. 4,580,036 for gas chromatography, U.S. Pat. No. 4,586,818 for photometry, U.S. Pat. No. 4,591,266 for optical spectroscopy and U.S. Pat. No. 4,629,320 for atomic absorption spectrometry. Such sample chambers include ports or other means for the introduction of sample liquids or gases and interior or exterior means to inspect the condition of the samples within the sample chambers.

SUMMARY OF THE INVENTION

Beginning with the algorithm for the expression of categorical syllogisms by means of numbers provided by Leibniz and substituting primary and complementary colors for his prime and non-prime numbers respectively, the categorical syllogism may be represented photonically. By then reducing the particular negative and particular affirmative cases to one representation, the entire relationship can be expressed in three dimensions within a regular rhombic dodecahedron.

Within the dodecahedron certain specific imaginary interior planes may be selected. In the regular rhombic dodecahedron the particular interior planes are square. The edges of the imaginary planes lie in the interior faces of the dodecahedron and according to the syllogism define the colors of the interior faces. In the preferred embodiment each interior face comprises a silver backed mirror having sufficient depth of color to act as a color filter of reflected light. As a complete "solid", the silvered backs form the exterior walls of the dodecahedron, the colored faces being directed toward the center of the "solid".

Depending upon the interior face viewed, the reflected light will be of a specifically filtered color. In a sample cell multiple colors can be viewed simultaneously assuming a suitable multi-chromatic light source within the cell. The chamber or cell is therefore useful for sample analysis wherein simultaneous photon absorption at specified frequencies is the mode of analysis of a fluid sample.

DESCRIPTION OF THE DRAWINGS

FIGS. 1, 2 and 3 are perspective views of a regular dodecahedron illustrating three imaginary interior planes, and FIGS. 4, 5 and 6 illustrate the three imaginary interior planes of the regular rhombic dodecahedron.

DESCRIPTION OF THE PREFERRED EMBODIMENTS

Illustrated in FIGS. 1, 2 and 3 is a dodecahedron presented as a transparent "solid" for purposes of clarity. The regular dodecahedron 10 pictured has twelve rhombic faces such as 12 of equal size with angles 14 at the acute vertices of 70°]32". In actual application the exterior is silvered to form inwardly directed mirrors of the faces enclosing a hollow cell or chamber within the "solid".

Each interior face is colored to form a colored mirror directed toward the center of the chamber. The colors are prescribed by three imaginary planes intersecting the acute vertices of three sets of four faces. In FIG. 1 the imaginary plane designated by the ghost line 16 intersects vertices 18, 20, 22 and 24. In so doing imaginary plane 16 bisects faces 26, 28, 30 and 32 to form a square also defined by the ghost line 16. The colors of the faces 26, 28, 30 and 32 so bisected are defined by the syllogism above to be yellow 26, green 28, cyan 30 and blue 32. The yellow face 26 directly faces the cyan face 30 and the green face 28 directly faces the blue face 32.

In a similar manner in FIG. 2 a second imaginary plane designated by the ghost line 34 intersects vertices 18, 36, 22 and 38. the imaginary plane 34 bisects faces 40, 42, 44 and 46 to form a square also defined by the ghost line 34. The colors of the faces 40, 42, 44 and 46 so bisected are defined to be red 40, magenta 42, green 44 and cyan 46. The red face 40 directly faces the green face 44 and the magenta face 42 directly faces the cyan face 46.

And in FIG. 3 a third imaginary plane designated by the ghost line 48 intersects vertices 20, 24, 36 and 38 and bisects planes 50, 52, 54 and 56. The colors of the faces 50, 52, 54 and 56 so bisected are defined to be blue 50, magenta 52, red 54 and yellow 56. The blue face 50 directly faces the red face 54 and the magenta face 52 directly faces the yellow face 56.

The three imaginary planes 16, 34 and 48 are shown respectively in FIGS. 4, 5 and 6. The four faces about each imaginary plane are as indicated by the reference numbers which also define the colors of the faces and correspond with the numbers in FIGS. 1, 2 and 3.

As suggested by the sensors 58 and 60 shown in FIG. 1, small sensors may be located in the interior wall to sense monochromatic light reflected from an opposite face. The sensors may include sources of monochromatic light directed at the opposite walls or a multispectral light 62 source may be located within the chamber and the faces constructed to act as monochromatic mirror filter surfaces. The sensors and multispectral or monochromatic light may be electro-optical or fiber optic for example. Retroreflective mirror surfaces may also be employed for a tightly collimated reflected beam from a combined sensor and source.

As an alternative to fully reflective surfaces on the interior, the faces may each be reflective to a particular monochromatic frequency and transparent to a different monochromatic frequency. Such a construction permits the sensors to be positioned exterior to the chamber as illustrated at 64 and 66 in FIG. 2. The sensors may also be located at the vertices as illustrated at 68 and 70 in FIG. 3.

Although only two sensors are illustrated in each of FIGS. 1, 2 and 3, many more sensors may be utilized. In particular, twelve sensors may be positioned opposite the twelve faces for simultaneous sensing of the monochromatic radiation from each mirrored surface. A port 72 to admit or withdraw a fluid or solid specimen is also shown in the figures.

The twelve optical sensors may be connected to a single computer programmed for sequential repetitive sampling or, alternatively, to twelve parallel processors for simultaneous repeated sampling of the sensors. High speed simultaneous sampling has application in the analysis of intermediate reaction products and short lived radicals produced and destroyed during a complex chemical reaction.

Although the chamber has been disclosed generally in terms of the visible light spectrum, the principles embodied are applicable to ultraviolet, infrared and other portions of the electromagnetic spectrum.

Calibration gases may also be introduced through port 72 to the chamber. In particular, the calibration gases may be an ion enriched carbon gas or a chromium gas.

I claim:

1. A chamber comprising a multifaceted rhombic dodecahedral interior wall, a plurality of the faces of the wall comprising reflective surfaces, the reflective surfaces each comprising distinct monochromatic reflective filters whereby distinct substantially monochromatic radiation is reflectable from each of said surfaces and wherein opposed surfaces are of primary and complementary radiative frequencies.

2. The chamber of claim 1 wherein six primary and complementary visible colors are arranged in opposed complementary pairs on the twelve interior faces of the dodecahedron.

3. The chamber of claim 1 wherein six primary and complementry visible colors are arranged in three sets of four colors on the twelve interior faces of the dodecahedron, each set of four colors being arranged in opposed complementary pairs on four faces defined by a single imaginary plane passing through the four vertices at the extremes of the four planes.

4. The chamber of claim 1 including multiple sensing means communicating with the interior of the chamber, each of said sensing means positioned to sense monochromatic radiation reflected from a particular one of the reflective surfaces.

5. The chamber of claim 4 including means to admit or withdraw a fluid from within the chamber.

6. The chamber of claim 4 including means to admit or remove a solid specimen from within the chamber.

7. The chamber of claim 1 wherein at least one reflective surface is at least partially transparent to the monochromatic radiation reflected from a face opposite said one reflective surface.

8. The chamber of claim 7 including at least one sensing means exterior to the chamber and positioned to sense the monochromatic radiation passing through said partially tranparent surface.

9. The chamber of claim 1 including a multispectral radiation source in communication with the interior of the chamber.

10. The chamber of claim 1 wherein at least one of said reflective surfaces is at least partially transparent to monochromatic radiation of a frequency different from the monochromatic frequency reflectable by said surface.

11. The chamber of claim 1 wherein the chamber contains an ion enriched carbon gas.

12. The chamber of claim 1 wherein the chamber contains a chromium gas.

13. The chamber of claim 1 wherein the chamber contains a calibration gas.

14. A chamber comprising a multifaceted rhombic dodecahedral interior wall, a plurality of the faces of the wall comprising reflective surfaces, the reflective surfaces comprising monochromatic reflective filters whereby distinct monochromatic radiation is reflectable from each of said reflective surfaces,
a plurality of sensing means each positioned to receive radiation reflected from a monochromatic reflective surface,
and means in communication with said sensing means to process information transmitted from said sensing means.

15. The chamber of claim 14 wherein the means in communication with the sensing means include a parallel processor comprising a plurality of microprocessors each one dedicated to an individual sensing means for simultaneous processing of information from the plurality of individual sensing means.

16. The chamber of claim 15 wherein the sensing means are in communication with the interior of the chamber.

17. The chamber of claim 15 wherein at least one reflective surface is at least partially transparent to the monochromatic radiation reflected from a face opposite said one reflective surface and the sensing means include at least one sensing means exterior to the chamber and positioned to sense the monochromatic radiation passing through said partially transparent surface.

18. The chamber of claim 17 wherein the means in communication with the sensing means include a parallel processor comprising a plurality of microprocessors each one dedicated to an individual sensing means for simulataneous processing of information from the plurality of individual sensing means.

19. The chamber of claim 14 including a multispectral radiation source in communication with the interior of the chamber.

20. The chamber of claim 14 wherein at least one of said reflective surfaces is retroreflective.

21. The chamber of claim 14 wherein the chamber contains a calibration gas.

* * * * *

UNITED STATES PATENT AND TRADEMARK OFFICE
CERTIFICATE OF CORRECTION

PATENT NO. : 4,799,794
DATED : January 24, 1989
INVENTOR(S) : Roy L. Mynatt

It is certified that error appears in the above-identified patent and that said Letters Patent is hereby corrected as shown below:

Correct the spelling of the Patentee's family name to read --Mynatt-- at the top of the Patent cover sheet and at [76] on the cover sheet.

Signed and Sealed this

Eleventh Day of July, 1989

Attest:

DONALD J. QUIGG

*Attesting Officer*   *Commissioner of Patents and Trademarks*